(12) United States Patent
Tabbara

(10) Patent No.: US 8,591,451 B2
(45) Date of Patent: Nov. 26, 2013

(54) SURGICAL METHODS, DEVICES, AND KITS

(76) Inventor: Marwan Tabbara, Miami, FL (US)

( * ) Notice: Subject to any disclaimer, the term of this patent is extended or adjusted under 35 U.S.C. 154(b) by 224 days.

(21) Appl. No.: 12/831,361

(22) Filed: Jul. 7, 2010

(65) Prior Publication Data

US 2011/0009802 A1 Jan. 13, 2011

Related U.S. Application Data

(60) Provisional application No. 61/223,440, filed on Jul. 7, 2009.

(51) Int. Cl.
*A61M 5/00* (2006.01)
*A61M 37/00* (2006.01)

(52) U.S. Cl.
USPC ............. 604/8; 604/6.05; 604/6.06; 604/6.16

(58) Field of Classification Search
USPC .................. 604/8, 6.05, 6.06, 6.16
See application file for complete search history.

(56) References Cited

U.S. PATENT DOCUMENTS

| | | | | |
|---|---|---|---|---|
| 2,453,056 A * | 11/1948 | Zack | ............................. | 606/153 |
| 3,254,650 A * | 6/1966 | Collito | ........................ | 606/153 |
| 3,540,451 A * | 11/1970 | Zeman | ............................ | 604/27 |
| 3,683,926 A | 8/1972 | Suzuki | | |
| 4,096,860 A * | 6/1978 | McLaughlin | ................... | 604/44 |
| 4,318,401 A * | 3/1982 | Zimmerman | .................. | 604/28 |
| 4,352,358 A * | 10/1982 | Angelchik | .................... | 606/155 |
| 4,366,819 A * | 1/1983 | Kaster | ........................... | 606/153 |
| 5,282,827 A * | 2/1994 | Kensey et al. | ................ | 606/215 |
| 5,324,306 A * | 6/1994 | Makower et al. | ............. | 606/213 |
| 5,366,462 A * | 11/1994 | Kaster et al. | ................... | 606/153 |
| 5,383,896 A * | 1/1995 | Gershony et al. | ............. | 606/213 |
| 5,759,194 A * | 6/1998 | Hammerslag | ................. | 606/214 |
| 5,797,920 A * | 8/1998 | Kim | ............................. | 606/108 |
| 5,843,124 A * | 12/1998 | Hammerslag | ................. | 606/214 |
| 5,928,253 A | 7/1999 | Sherman | | |
| 5,947,919 A * | 9/1999 | Krueger et al. | ................... | 604/8 |
| 5,984,955 A * | 11/1999 | Wisselink | ..................... | 623/1.35 |
| 6,017,352 A * | 1/2000 | Nash et al. | ..................... | 606/153 |
| 6,074,416 A * | 6/2000 | Berg et al. | ..................... | 623/1.36 |
| 6,110,188 A * | 8/2000 | Narciso, Jr. | .................... | 606/153 |
| 6,171,319 B1 * | 1/2001 | Nobles et al. | .................. | 606/151 |
| 6,193,734 B1 * | 2/2001 | Bolduc et al. | ................. | 606/153 |
| 6,210,365 B1 * | 4/2001 | Afzal | ........................ | 604/101.03 |
| 6,248,117 B1 * | 6/2001 | Blatter | ........................... | 606/153 |
| 6,461,320 B1 * | 10/2002 | Yencho et al. | ..................... | 604/8 |
| 6,488,662 B2 * | 12/2002 | Sirimanne | ................ | 604/164.01 |
| 6,551,334 B2 | 4/2003 | Blatter | | |
| 6,582,409 B1 | 6/2003 | Squitieri | | |
| 6,656,151 B1 * | 12/2003 | Blatter | ........................ | 604/96.01 |
| 6,746,459 B2 * | 6/2004 | Kato | ............................... | 606/153 |
| 6,814,718 B2 | 11/2004 | McGuckin | | |
| 6,843,795 B1 * | 1/2005 | Houser et al. | ................. | 606/153 |
| 6,884,251 B2 * | 4/2005 | Spence et al. | ................. | 606/153 |
| 6,899,718 B2 * | 5/2005 | Gifford et al. | ................ | 606/155 |
| 6,905,481 B2 * | 6/2005 | Sirimanne | ................ | 604/164.01 |
| 6,984,238 B2 * | 1/2006 | Gifford et al. | ................. | 606/155 |
| 7,008,412 B2 | 3/2006 | Maginot | | |
| 7,112,211 B2 * | 9/2006 | Gifford et al. | ................. | 606/153 |
| 7,118,546 B2 * | 10/2006 | Blatter | ......................... | 604/6.16 |
| 7,124,570 B2 * | 10/2006 | Blatter et al. | ................. | 604/6.16 |
| 7,131,959 B2 * | 11/2006 | Blatter et al. | ................. | 604/6.16 |
| 7,303,569 B2 * | 12/2007 | Yencho et al. | ................. | 606/153 |
| 2002/0173808 A1 * | 11/2002 | Houser et al. | .................. | 606/153 |
| 2002/0173809 A1 * | 11/2002 | Fleischman et al. | .......... | 606/153 |
| 2003/0014063 A1 | 1/2003 | Houser | | |
| 2003/0055371 A1 | 3/2003 | Wolf | | |
| 2003/0100920 A1 | 5/2003 | Akin | | |
| 2004/0097973 A1 * | 5/2004 | Loshakove et al. | ........... | 606/144 |
| 2005/0149078 A1 * | 7/2005 | Vargas et al. | .................. | 606/153 |
| 2005/0267498 A1 * | 12/2005 | Hendricksen et al. | ........ | 606/153 |
| 2006/0155313 A1 * | 7/2006 | Yencho et al. | ................. | 606/153 |
| 2007/0073343 A1 * | 3/2007 | Jahns et al. | .................... | 606/232 |
| 2007/0073344 A1 * | 3/2007 | Jahns et al. | .................... | 606/232 |
| 2007/0179589 A1 * | 8/2007 | Williams et al. | ............. | 623/1.13 |
| 2007/0249986 A1 | 10/2007 | Smego | | |
| 2012/0083808 A1 * | 4/2012 | Shriver | ......................... | 606/153 |

FOREIGN PATENT DOCUMENTS

EP 1955664 8/2008
WO 9965409 12/1999

OTHER PUBLICATIONS

Bioconnect Systems, <<http://www.bioconnectsystems.com>> (last visited on Oct. 7, 2010).

\* cited by examiner

*Primary Examiner* — Tatyana Zalukaeva
*Assistant Examiner* — Guy K Townsend
(74) *Attorney, Agent, or Firm* — Cuenot, Forsythe & Kim, LLC; Stanley A. Kim

(57) ABSTRACT

Methods, devices, and kits for creating bloodstream access in patients are provided. A patient's vessel is accessed surgically and blood flow is stopped. A short incision is made through the wall of one side of the vessel where the blood flow was stopped. A puncturing instrument is pushed through the incision across the lumen and through the vessel wall at a site opposite the incision. After the puncturing instrument is removed, a vessel wall traversing device which can be shaped like a blunt-ended nail with a hollow shank and a head of a larger diameter than the shank is inserted in the puncture hole blunt end first such that the shank traverses the puncture hole with the blunt end being positioned exterior to the outer surface of the vessel and the head of the device abutting inner surface of the vessel at the puncture hole. The portion of the shank that projects outwards from the vessel wall is connected to one end of a flexible cannula, and the other end of the cannula is passed through the surrounding tissue such that the end of the cannula opposite the vessel wall traversing device protrudes through the skin of the patient. A portion of the cannula protruding from the patient is clamped off, the incision is closed, and blood flow is restored to the vessel. Blood within the vessel is than accessible via the portion of the cannula protruding from the patient.

9 Claims, 4 Drawing Sheets

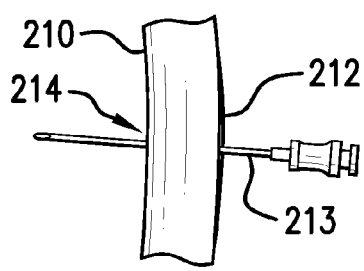
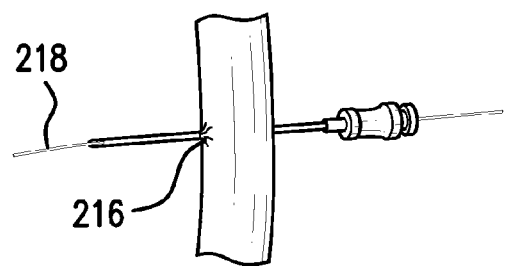
FIG.2A  FIG.2B
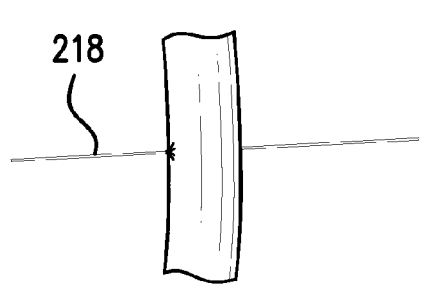
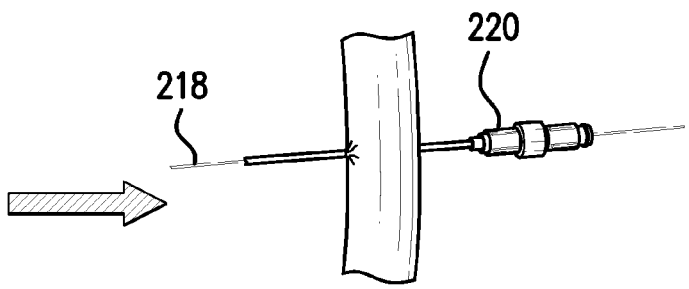
FIG.2C  FIG.2D
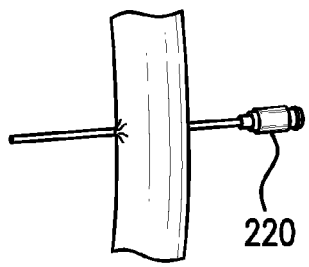
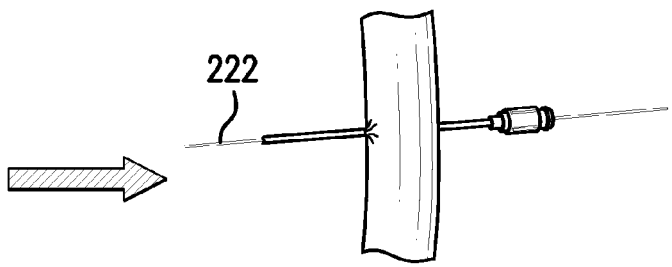
FIG.2E  FIG.2F
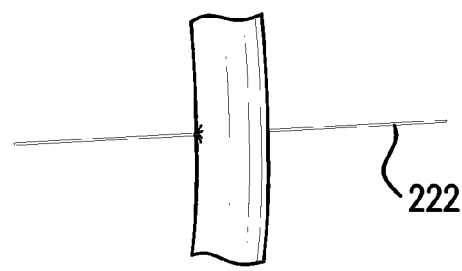
FIG.2G

US 8,591,451 B2

SURGICAL METHODS, DEVICES, AND KITS

CROSS-REFERENCE TO RELATED APPLICATIONS

The present application claims the priority of U.S. provisional patent application Ser. No. 61/223,440 filed on Jul. 7, 2009, which is incorporated herein by reference.

STATEMENT AS TO FEDERALLY SPONSORED RESEARCH

Not applicable.

FIELD OF THE INVENTION

The invention relates generally to the fields of medicine, medical devices, and vascular surgery. More particularly, the invention relates to methods and devices for creating vascular access, e.g., for hemodialysis during the surgery for creating an ateriovenous (AV) fistula.

BACKGROUND

In renal failure patients, poor kidney function results in the accumulation of waste products and excess water in the blood. Hemodialysis uses an "artificial kidney" to remove these waste products and excess water from a patient's blood. In this procedure, the patient's blood is flowed over one side of a semi-permeable membrane while a dialysate is flowed in an opposite direction on the other side of the membrane. Osmotic pressure causes the waste products and excess water to selectively flow across the membrane into the dialysate to reduce their concentration in the patient's blood.

Over the last several decades numerous technological improvements have made this procedure safer and more effective. Nonetheless, because a large amount of blood must be transferred between a patient and a dialysis machine, it remains subject to complications such as infection and bleeding. It is also inconvenient to patients as it requires about 2-4 visits to a dialysis center each week.

To reduce complications and inconvenience, a number of methods and devices have been developed which facilitate repeated access to a patient's blood. These include intravenous catheters, synthetic grafts, and AV fistulas. Most dialysis patients receive dialysis using AV fistulas or AV grafts (made of heterologous material such as plastic, PTFE, or animal arteries). Because both fistulas and grafts must heal or mature prior to use, when most patients in urgent need of dialysis first present at a clinic, access to the bloodstream is obtained by tunneling silicone catheters through the superior vena cava via a small incision in the neck into an area adjacent to the right atrium of the heart. The end of the catheter opposite the atrium is then tunneled through the chest tissue to an exit site in the skin where it can be accessed.

While effective, tunneled catheters are also subject to serious complications. The main problem with placing the tunneled catheters in the heart is that the catheter itself can cause scarring of veins leading to stenosis (central vein stenosis)—particularly in patients having multiple catheter placements over many years and in those who develop catheter infections. Patients with catheter-related central vein stenosis are often unable to utilize fistulas or grafts because the stenosis impedes the flow of blood back from the fistulas or grafts and causes severe swelling of the limb where the fistula or graft was created. Long-term use of tunneled catheters almost always causes infection at the catheter placement site so is not practical. Accordingly, many patients with catheter-related central vein stenosis die because surgeons can no longer create a long-term access site.

SUMMARY

The invention relates to the development of new methods, devices, and kits for creating bloodstream access in patients. In an exemplary method of the invention, a patient's vessel (e.g., vein) is accessed surgically and blood flow is stopped using one or more vascular clamps. A short incision is made through the wall of one side of the vessel where the blood flow was stopped. A puncturing instrument such as a micropuncture needle is then pushed through the incision across the lumen and through the vessel wall at a site opposite the incision. After the puncturing instrument is removed, a vessel wall traversing device shaped like a blunt-ended nail with a hollow shank (e.g., with a bore extending the entire length of the shank) and a head of a larger width than the shank and the diameter of the puncture hole is inserted in the puncture hole blunt end first such that the shank traverses the puncture hole with the blunt end being positioned exterior to the outer surface of the vessel and the head of the device abutting inner (lumenal) surface of the vessel at the puncture hole. The portion of the shank that projects outwards from the vessel wall is connected to one end of a flexible cannula such as a Tesio catheter, and the other end of the cannula is passed through the surrounding tissue such that the end of the cannula opposite the vessel wall traversing device protrudes through the skin of the patient. A portion of the cannula protruding from the patient is clamped off, the incision is closed, and blood flow is restored to the vessel by removing the hemostat(s). Blood within the vessel is than accessible via the portion of the cannula protruding from the patient.

In one adaptation of the invention, immediate vascular access (e.g., for urgent hemodialysis) is provided without requiring a tunneling central catheter. In this adaptation, bloodstream access as described above is created during the same surgery used to create an AV fistula. vein is connected to an artery, i.e., a fistula is created. Starting at least 2 cm from the connection or anastomosis, two incisions of about 5 (e.g., 3, 4, 5, 6, or 7) mm long are made lengthwise (i.e., longitudinal, parallel to the long axis of the vein) through the wall of the vein being used to create the fistula. The incisions are spaced at least about 5 (e.g., 4.5, 5, 6, 7, 8, 9 or 10) cm apart to avoid possible recirculation of the blood when the intake is too close to the return.

A vessel wall traversing device is positioned in the vessel wall at sites opposite each incision as described above. Tubing that extends through the skin can be connected to each vessel wall traversing device in order to provide access points for hemodialysis. While the fistula is maturing, blood can be accessed through the tubing/vessel wall traversing devices. Once the fistula matures, this process can be discontinued in lieu of regular fistula access.

The invention thus provides an alternative to tunneled right atrial catheterization and prevents the complications associated therewith. A significant advantage of this new procedure is that the problems associated with tunneling catheters is entirely avoided and the patient, who might otherwise never receive procedures other than placement of a tunneling catheter, ends up with an AV fistula that can provide repeated long-term bloodstream access.

Accordingly, the invention features a method for creating bloodstream access in an animal subject (e.g., a human being). The method can include one or more of the steps of: (a) accessing a vessel of the subject surgically; (b) stopping blood flow in a portion of the vessel; (c) making an opening through the wall of one side of the vessel within the portion where the blood flow was stopped; (d) creating a puncture hole in the vessel wall at a site opposite the opening; (e) inserting into the puncture hole a vessel wall traversing device with a first end positioned in the lumen of the vessel and a second end projecting outwardly from the vessel wall; (f) connecting the second end of the vessel wall traversing device to one end of a cannula; (g) positioning the other end of the cannula so that it protrudes through the skin of the subject; (h) clamping a portion of the cannula protruding from the subject; (i) closing the incision; (j) restoring blood flow to the vessel; and (k) accessing blood within the vessel via the portion of the cannula protruding from the subject. For applications such as hemodialysis, the steps (a)-(k) can be performed twice on the vessel to yield two access sites. The steps (a)-(k) might also be performed during a surgical operation to create an AV fistula.

The invention also includes a vessel wall traversing device. The vessel wall traversing device can be shaped like a blunt-ended nail with a hollow shank having a bore through its length and a head of a larger diameter than the shank, and can be positioned on the vessel such that the shank traverses the puncture hole, the blunt end is positioned exterior to the outer surface of the vessel, the head abuts the inner surface of the vessel at the puncture hole, and the shank projects outwards from the vessel wall. The shank can have a length of between about 4-12 mm and a width of between about 1-4 mm; the head can have a width of between about 2-6 mm and a length between about 0.7-3 mm; and the bore can have a diameter of between about 0.8-1.3 mm. The vessel wall traversing device can be sterile, and include a biocompatible plastic, an antimicrobial agent, and/or an anti-thrombogenic agent.

In another aspect, the invention features a kit that includes a hermetically sealed container housing the sterile vessel wall traversing device described above or elsewhere herein. The container can, in some cases, further include an applicator which is reversibly attached to the vessel wall traversing device.

Unless otherwise defined, all technical terms used herein have the same meaning as commonly understood by one of ordinary skill in the art to which this invention belongs. Commonly understood definitions in surgery can be found in Steadman's Surgery Words, S. Kovacs (ed.), Williams & Wilkins, 1997.

Although methods and materials similar or equivalent to those described herein can be used in the practice or testing of the present invention, suitable methods and materials are described below. All publications mentioned herein are incorporated by reference in their entirety. In the case of conflict, the present specification, including definitions will control. In addition, the particular embodiments discussed below are illustrative only and not intended to be limiting.

BRIEF DESCRIPTION OF THE DRAWINGS

FIGS. 2A-M is a series of highly schematic illustrations of a surgical procedure of the invention.

DETAILED DESCRIPTION

The invention encompasses methods, devices, and kits for creating a bloodstream access site in patients. The below described preferred embodiments illustrate adaptation of these methods, devices, and kits. Nonetheless, from the description of these embodiments, other aspects of the invention can be made and/or practiced based on the description provided below.

Methods involving conventional surgical techniques are described herein. Such techniques can be practiced by qualified surgeons and are also described in Way and Doherty, Current Surgical Diagnosis and Treatment, McGraw-Hill/Appleton & Lange, 11th edition (Sep. 24, 2002). Vascular surgical techniques are described in more detail in Rutherford's Textbook on Vascular Surgery, 5th ed., Robert B. Rutherford, WB Saunders Co., 2000.

Figure 1:
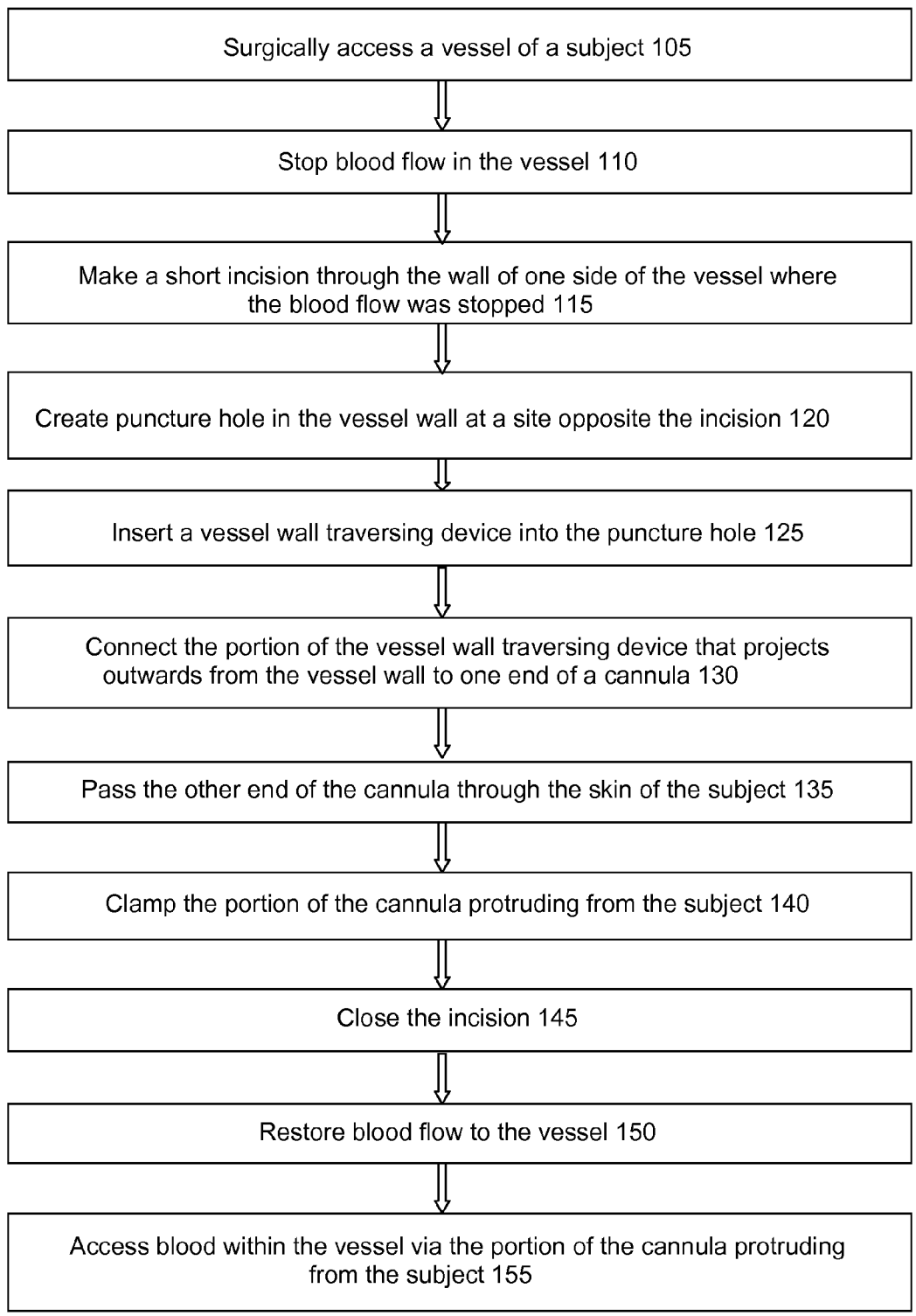
FIG. 1 is a flowchart showing steps in one method of the invention.

In one aspect, referring now to FIG. 1, the invention features a method for creating bloodstream access in an animal subject. This method can include one or more (1, 2, 3, 4, 5, 6, 7, 8, 9, 10, 11, 12, or 13) of the following steps: (a) a step of surgically accessing a vessel of the subject 105, (b) a step of stopping blood flow in the vessel 110; (c) a step of making a short incision through the wall of one side of the vessel where the blood flow was stopped 115, (d) a step of puncturing the vessel wall at a site opposite the incision to create a puncture hole 120, (e) a step of inserting into the puncture hole a vessel wall traversing device 125, (f) a step of connecting the portion of the vessel wall traversing device that projects outwards from the vessel wall to one end of a cannula 130, (g) a step of passing the other end of the cannula through the skin of the subject 135, (h) a step of clamping the portion of the cannula protruding from the subject 140, (i) a step of closing the incision 145, (j) a step of restoring blood flow to the vessel 150, and (k) a step of accessing blood within the vessel via the portion of the cannula protruding from the subject 155.

The steps (a)-(k) 105, 110, 115, 120, 125, 130, 135, 140, 145, 150, 155 can be performed twice on the same vessel at different sites to allow in and out access for hemodialysis. They can also be performed during a surgical operation to create an arteriovenous fistula. For example, an AV fistula (e.g., a radiocephalic fistula) is created by surgically connecting a vein to an artery. Blood flow is allowed to pass through the fistula making sure that the fistula is working well and determining that the vein is well-positioned and not kinked. Blood flow from the artery just beyond the anastomosis is then stopped by placing a vascular clamp on the vein just beyond the anastomosis. Another clamp is placed around 7-8 cm away from the first clamp still on the vein to isolate an adequate length of the vein without any blood in it to allow placement of two devices separated around 5 (4, 5, 6, 7, 8, 9, or 10+/−0.5) cm from each other.

Figure 2H:
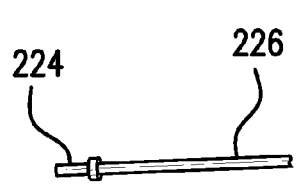

Referring now to FIGS. 2A-2M, a representative method for creating bloodstream access from a vessel 210 (e.g., a vessel 210 or fistula) is shown. In FIG. 2A, an incision or other type of opening 212 of about 5 (3, 4, 5, 6, 7, 8, 9, or 10+/−0.5) mm in length is made in a longitudinal fashion (lengthwise, parallel to the long axis of the vessel 210) in the vessel 210, and a puncturing device 213 such as a micropuncture needle (e.g., 19, 20, 21, 22, 23, or 24 gauge) is inserted through the opening 212 and pushed through the wall of the vessel 210 to create a puncture hole 216 in the vessel 210 at a site 214 opposite the opening 212. In FIGS. 2B and 2C, a first guide 218 such as a 0.018 wire guide is passed through the bore of the puncturing device 213 and the puncturing device 213 is removed such that the first guide 218 traverses the opening 212 and puncture hole 216 in the side of the vessel 210 opposite the opening 212.

As shown in FIG. 2D, a first catheter with sheath and inner dilator 220 such as a 4F coaxial exchange catheter (4F sheath with a 3F inner dilator) is threaded over the first guide 218 through the opening 212 and puncture hole 216. The inner dilator of catheter 220 and the first guide 218 are removed (FIG. 2E) and a second guide 222 having a diameter larger than the first guide 218 (e.g., a 0.035 wire guide) is inserted through the sheath of the first catheter 220 such that the second guide 222 in the sheath of the first catheter 220 traverses the opening 212 and puncture hole 216 as shown in FIG. 2F. The sheath of the first catheter 220 is then removed leaving the second guide 222 positioned through the opening 212 and puncture hole 216 as shown in FIG. 2G.

Figure 2I:
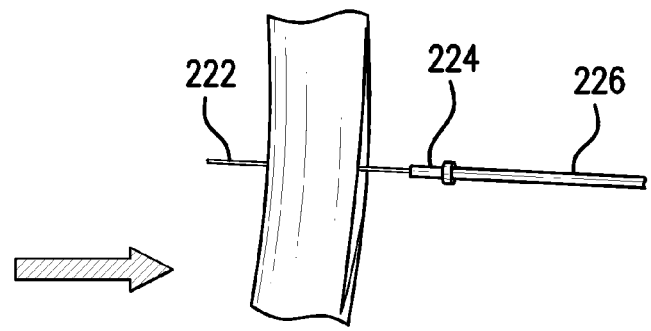
Figure 2J:
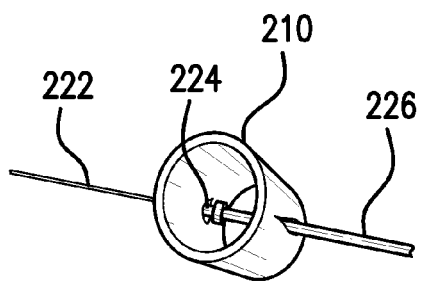

Referring now to FIG. 2H, a vessel wall traversing device 224 having a longitudinal bore is provided, and positioned on an applicator 226 which has an end adapted to fit a portion of the vessel wall traversing device 224. The applicator can be any suitable device such as a 3, 4, 5, 6, or 7F stiff dilator. In FIG. 2I, the end of the second guide 222 extending out of the opening 212 is threaded through the bore of the vessel wall traversing device 224 and the attached applicator 226. As shown in FIGS. 2I and 2J, the vessel wall traversing device 224 with attached applicator 226 is pushed through the opening 212, through the lumen of the vessel 210, and then through the wall of the vessel 210 opposite the opening 212 such that the vessel wall traversing device 224 is securely positioned in the puncture hole 216 in the vessel 210 wall (e.g., for the particular vessel wall traversing device 224 shown in the figures, with the shank portion of the vessel wall traversing device protruding through vessel 210 wall and head portion preventing the vessel wall traversing device 224 from moving through the wall of vessel 210).

Figure 2K:
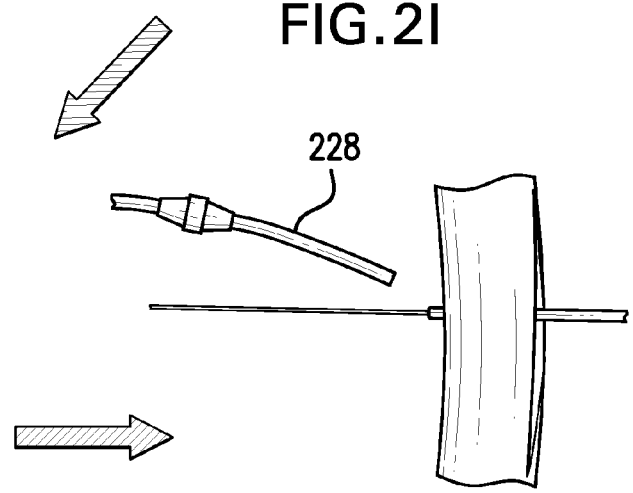
Figure 2L:
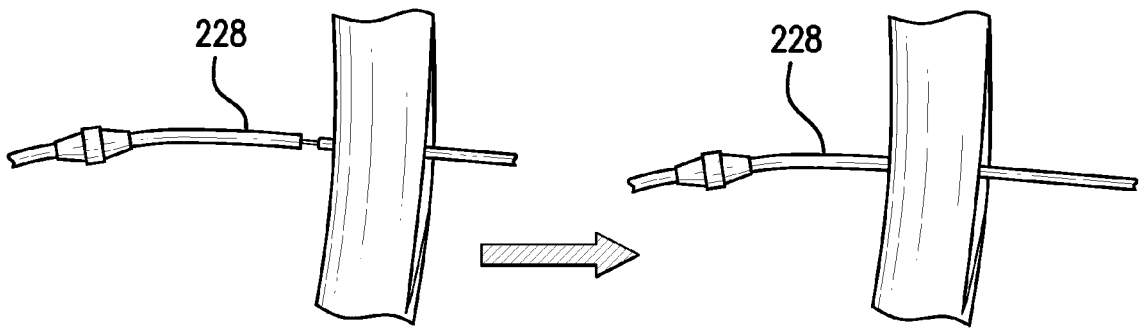
Figure 2M:
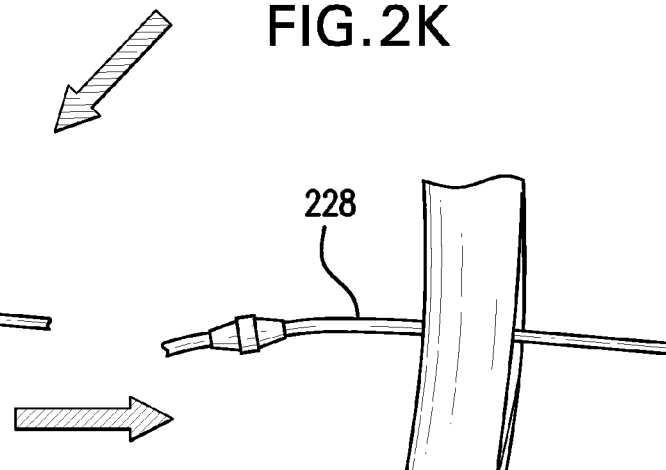

With the second guide 222 still threaded through the applicator 226 and the vessel wall traversing device 224, referring to FIGS. 2K, 2L, and 2M, a second catheter 228 such as a modified Tesio catheter is threaded over the end of the second guide 222 opposite the opening 212 and its end is attached to the vessel wall traversing device 224 (e.g., threaded into the shank portion of the particular vessel wall traversing device 224 shown in the figures) and pushed until the wall of vessel 210 is sandwiched between the tip of the second catheter 228 and the head portion of the vessel wall traversing device 224. The applicator 226, second catheter 228, and second guide 222 are then removed, and the opening 212 is closed and blood flow in the vessel 210 is restored. The other end of the second catheter 228 is pulled out through the skin of the patient (in the case of a Tesio catheter, such that the cuff is just underneath the skin). A hub is then connected to the end of the second catheter 228 protruding from the skin to allow the second catheter 228 to be flushed and clamped closed. Access to blood in the vessel 210 can be performed through the second catheter 228 or hub (e.g., in the case of hemodialysis, the dialysis tubing can be connected to the hub).

For hemodialysis, the foregoing procedure can be repeated to create two blood access devices in the same vessel, and this can also be performed in conjunction with a procedure to create an AV fistula. In this case, a catheter and/or hub closer to the artery can be colored red and is used to withdraw the blood to the hemodialysis machine and the other catheter and/or hub can be colored blue and is used to return the blood to the vessel.

One or more of the components described above can be included in a kit. These components might also be sterilized and contained within hermetically sealed packaging such as easy-open, peel-apart packaging. For example, the vessel wall traversing device 224 and the applicator 226 might be sterilized, pre-fastened together, and/or contained within a single easy-open, peel-apart package. A kit might also include a plurality (e.g., 2, 3, 4, 5, 6, 7, 8, 9, 10, or more) of different sized and/or shaped vessel wall traversing devices from which a surgeon could select from for a given surgery.

Figure 3:
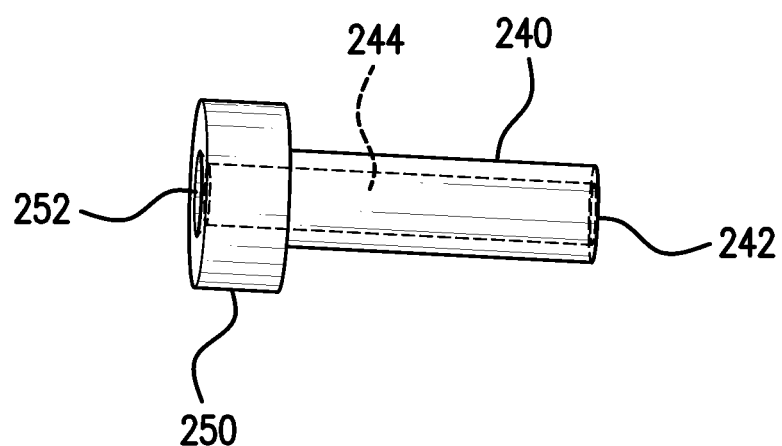
FIG. 3 is a perspective view of a vessel wall traversing device of the invention.

One version of the vessel wall traversing device 224 is shown in FIG. 3. In this version, the vessel wall traversing device 224 is shaped like a blunt-ended nail with a rod-shaped shank 240, a head 250 of a larger width than the shank 240 (to secure the device 224 in a vessel wall by preventing the head 250 from passing through the puncture hole 216), and a bore 244 running longitudinally through the center of the shank 240 and head 250. Although other dimensions are possible, for typical applications, the shank 240 can have a length of between about 4-12 mm (e.g., 4, 5, 6, 7, 8, 9, 10, 11, or 12+/−0.1, 0.2, 0.3, 0.4, or 0.5 mm) and a width of between about 1-4 mm (e.g., 1, 2, 3, or 4+/−0.1, 0.2, 0.3, 0.4, or 0.5 mm); the head 250 can have a width of between about 2-6 mm (e.g., 2, 3, 4, 5, or 6+/−0.1, 0.2, 0.3, 0.4, or 0.5 mm) or at least 0.5, 1, 2, 3, or 4 mm greater than the width of the shank 240, and a length between about 0.7-3 mm (e.g., 0.7, 0.8, 0.9, 1, 2, or 3+/−0.1, 0.2, 0.3, 0.4, or 0.5 mm); and the bore 244 can have a diameter of between about 0.8-1.3 mm (e.g., 0.8, 0.9, 1.0, 1.1, 1.2, or 1.3+/−0.01, 0.02, 0.03, 0.04, or 0.05 mm).

At each end of the bore 244 are apertures 242, 252. The aperture 252 at the head 250 of the device 224 can be shaped and sized to accept tight insertion of the applicator 226 [e.g., a 5F (or 3-7F) dilator]. The aperture 242 at the shank 240 of the device 224 can be shaped and sized to accept the second catheter 228 (e.g., a Tesio catheter). The vessel wall traversing device 224 can be made of any suitable material such as a biocompatible plastic. Suitable biocompatible plastics include materials such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art. The material may also be radiopaque. The material may have a hardness of at least about 75-A (e.g., at least 70, 75, 80, 85, 90, or 95-A) on a Shore durometer scale. The vessel wall traversing device 224 can be sterile, include an antimicrobial agent (e.g., a silver coating, a nitrofurazone coating, antimicrobial polymers, and/or nanoparticles), and/or include an anti-thrombogenic agent such as a heparin, hirudin-based coating.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, the methods and devices described above could be adapted to allow continuous monitoring of blood components such as glucose and/or controlled administration of medications such as insulin using sensors and pumps.

What is claimed is:

1. A method for creating bloodstream access in an animal subject, the method comprising the steps of:
   (a) accessing a vessel of the subject surgically;
   (b) stopping blood flow in a portion of the vessel;
   (c) making an opening through the wall of one side of the vessel within the portion where the blood flow was stopped;
   (d) creating a puncture hole in the vessel wall at a site opposite the opening;
   (e) inserting into the puncture hole a vessel wall traversing device with a first end positioned in the lumen of the vessel and a second end projecting outwardly from the vessel wall, wherein the vessel wall traversing device is shaped like a blunt-ended nail with a hollow shank having a bore through its length and a head of a larger diameter than the shank;
   (f) connecting the second end of the vessel wall traversing device to one end of a cannula;
   (g) positioning the other end of the cannula so that it protrudes through the skin of the subject;
   (h) clamping a portion of the cannula protruding from the subject;
   (i) closing the incision;
   (j) restoring blood flow to the vessel; and
   (k) accessing blood within the vessel via the portion of the cannula protruding from the subject.

2. The method of claim 1, wherein steps (a)-(k) are performed twice on the vessel.

3. The method of claim 1, wherein steps (a)-(k) are performed during a surgical operation to create an arteriovenous fistula.

4. The method of claim 1, wherein the vessel wall traversing device is positioned on the vessel such that the shank traverses the puncture hole, the blunt end is positioned exterior to the outer surface of the vessel, the head abuts the inner surface of the vessel at the puncture hole, and the shank projects outwards from the vessel wall.

5. The method of claim 1, wherein the shank has a length of between about 4-12 mm and a width of between about 1-4 mm; the head has a width of between about 2-6 mm and a length between about 0.7-3 mm; and the bore has a diameter of between about 0.8-1.3 mm.

6. The method of claim 1, wherein the vessel wall traversing device is inserted into the puncture hole using an applicator that reversibly attaches to the vessel wall traversing device.

7. The method of claim 1, wherein the vessel wall traversing device comprises a biocompatible plastic.

8. The method of claim 1, wherein the vessel wall traversing device comprises an anti-microbial agent.

9. The method of claim 1, wherein the vessel wall traversing device comprises an anti-thrombogenic agent.

* * * * *